United States Patent [19]

Bachalo

[11] Patent Number: 4,854,705
[45] Date of Patent: Aug. 8, 1989

[54] METHOD AND APPARATUS TO DETERMINE THE SIZE AND VELOCITY OF PARTICLES USING LIGHT SCATTER DETECTION FROM CONFOCAL BEAMS

[75] Inventor: William D. Bachalo, Los Altos Hills, Calif.

[73] Assignee: Aerometrics, Inc., Sunnyvale, Calif.

[21] Appl. No.: 177,630

[22] Filed: Apr. 5, 1988

[51] Int. Cl.⁴ ...................... G01N 15/14; G01N 21/47
[52] U.S. Cl. ..................................... 356/336; 356/338
[58] Field of Search .................. 356/336, 338; 250/574

[56] References Cited

U.S. PATENT DOCUMENTS

| | | | |
|---|---|---|---|
| 3,915,572 | 10/1975 | Orloff | 356/106 |
| 3,941,477 | 3/1976 | Schodl | 356/28 |
| 4,140,395 | 2/1979 | Kreikebaum | 356/336 |
| 4,179,218 | 12/1979 | Erdmann et al. | 356/336 |
| 4,329,054 | 5/1982 | Bachalo | 356/336 |
| 4,348,111 | 9/1982 | Goulas et al. | 356/336 |
| 4,387,993 | 6/1983 | Adrian | 356/336 |
| 4,444,450 | 4/1984 | Flinsenberg et al. | 356/336 |
| 4,492,467 | 1/1985 | Drain et al. | 356/336 |
| 4,537,507 | 8/1985 | Hess | 356/336 |
| 4,540,283 | 9/1985 | Bachalo | 356/336 |
| 4,636,075 | 1/1987 | Knollenberg | 356/336 |
| 4,701,051 | 10/1987 | Buchhave et al. | 356/336 |

OTHER PUBLICATIONS

Heterodyne and Quasi–Heterodyne Holographic Interferometry; Dandliker & Thalmann, 24 Opt. Eng. 824, (1985).
Heterodyne Holography Applications in Studies of Small Components, Pryputniewicz; 24 Opt. Eng. 849, (1985).
Phase/Doppler Spray Analyzer for Simultaneous Measurements of Drop Size and Velocity Distributions; Bachalo & Hauser; 23 Opt. Eng. 583, (1984).

(List continued on next page.)

Primary Examiner—Davis L. Willis
Assistant Examiner—Matthew W. Koren
Attorney, Agent, or Firm—Blakely, Sokoloff, Taylor & Zafman

[57] ABSTRACT

An apparatus for sizing particles, droplets, bubbles, or the like employing laser light scattering is disclosed. A laser is used for generating two beams of light having different wavelengths or polarizations. The beams with different wavelengths may be generated by an argon ion laser or by two different lasers (e.g., Helium Neon and Helium Cadmium). Two beams with orthogonal polarizations may be produced by partitioning a single linearly polarized beam and rotating the polarization of one by 90°. One of the beams is then expanded using a conventional beam expander and then redirected to be coaxial with the first beam. The beams are then focused to a common focal region. One beam is from two to four times larger in diameter than the other. An optical collection apparatus for sensing the light scattered caused by the particles, droplets, bubbles or the like passing through the focused beams has an axis extending into the focused beams. The axis of the collection apparatus may be aligned with the transmitted beams in the forward or backward direction (on-axis detection) or at some suitable angle to the beams (off-axis detection). The collection apparatus includes receiver lenses which focuses the scattered light through the beam splitter onto a first photo-detector, and light reflected from the beam splitter is directed onto a second photo-detector. The photo-detectors sense the scattered light from the beams with separate wavelengths or polarizations and produce proportionate voltage amplitudes. The peak voltages are determined from the information sensed by the light collection apparatus. A mathematical formulation is used with the known beam diameters and intensities along with the two measured signal voltage amplitudes to determine the particle trajectory through the beams and hence, particle size. The technique also allows for the determination of the sample volume cross-section and particle speed, thus allowing the determination of particle number density and volume flux.

28 Claims, 6 Drawing Sheets

OTHER PUBLICATIONS

Development of the Phase/Doppler Spray Analyzer for Liquid Drop Size and Velocity Characterizations; Bachalo & Houser; AIAA/SAE/ASME 20th Joint Propulsion Conf., (1984).

MIE and Refraction Theory Comparison for Particle Sizing with the Laser Velocimeter; Pendleton; 21 App. Opt. 684, (1982).

Method for Measuring the Size and Velocity of Spheres by Dual-Beam Light-Scatter Interferometry; Bachalo; 19 App. Opt. 363, (1980).

Particle Sizing Using Laser Interferometry; Roberds; 16 App. Opt. 1861, (1977).

Scattering from a Moving Spherical Particle by Two Crossed Coherent Plane Waves; Chu & Robinson; 16 App. Opt. 619, (1977).

Laser Doppler Measurements in Two-Phase Flows; Durst & Zare; Proc. of the LDA-Symposium Copenhagen 403, (1975).

Diffraction Analysis of Doppler Signal Characteristics for a Cross-Beam Laser Doppler Velocimeter; Robinson & Chu; 14 App. Opt. 2177, (1975).

High Resolution Hologram Interferometry by Electronic Phase Measurement; Dandliker, Ineichen & Mottier; 9 Opt. Comm. 412, (1973).

Interference Phase Measurement; Crane; 8 App. Opt. 538, (1969).

Heterodyne Holographic Interferometry; Dandliker; Progress in Optics, vol. XVII, (E. Wolf ed. 1980).

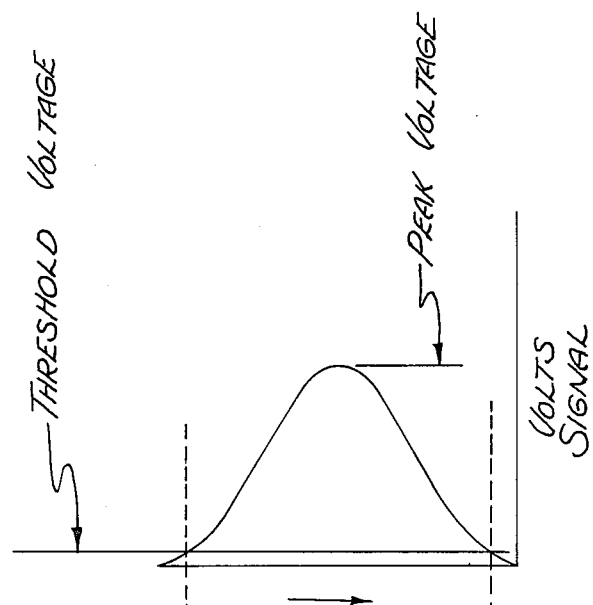
Fig. 6
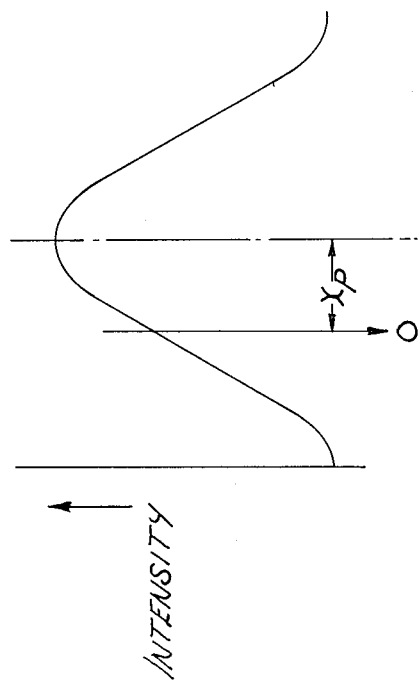
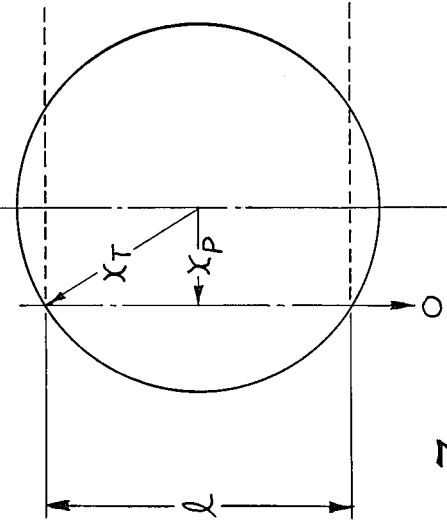
Fig. 7

METHOD AND APPARATUS TO DETERMINE THE SIZE AND VELOCITY OF PARTICLES USING LIGHT SCATTER DETECTION FROM CONFOCAL BEAMS

This invention was made with United States Government support under AFOSR contract F49620-86-C-0078 awarded by the Air Force. The Government has certain rights in this invention.

BACKGROUND OF THE INVENTION

1. Field of the Invention

The present invention relates to the field of determining the size, speed, and other parameters of particles, droplets, bubbles, or the like using laser light scattering.

2. Art Background

The measurement of particles, aerosols, liquid drops, bubbles and the like associated with industrial processes, atmospheric monitoring, combustion processes, agricultural applications of chemicals, cavitation studies, and the like has long been of importance. There have been a number of techniques developed that employ laser light scattering to determine the size of particles, drops, bubbles, or the like (hereinafter collectively referred to as "particles"). These techniques utilize one or more of a number of physical phenomena associated with the light scattering to obtain a measurable quantity that may be related to the particle size. The phenomena include the amplitude or intensity, the angular distribution, and the phase shift of the scattered light. Laser light extinction may also be used with other parameters to obtain additional information on the particles. Systems using the phase shift of the scattered light have been described by the inventor, W. D. Bachalo, in articles entitled, "Method for Measuring the Size and Velocity of Spheres by Dual-Beam Light-Scatter Interferometry", Applied Optics, Vol. 19, Feb. 1, 1980; "Phase/Doppler Spray Analyzer for Simultaneous Measurements of Drop Size and Velocity Distributions", and U.S. Pat. No. 4,540,283. Methods using the angular distribution of the scattered light have been described by J. Swithenbank, J. M. Beer, D. S. Taylor, D. Abbott, and G. C. McCreath, "Laser Diagnostic Technique for the Measurement of Droplet and Particle Size Distribution", *Progress in Astronautics and Aeronautics*, Vol. 53, ed., B. T. inn, 1977; and, E. D. Hirleman and S. Wittig, "In Situ Optical Measurement of Automobile Exhaust Gas Particulate Size Distributions: Regular Fuel and Methanol Mixtures", 16th Symposium (International) on Combustion, MIT, August 1976.

In the present disclosure, the system described utilizes the detection of the amplitude (intensity) of the light scattered by particles to obtain a measurement of their size and speed. The light scattered may be related to the particle size using the well-known Mie theory if the particles are homogeneous and spherical. Calibration with particles of known size may also be used to obtain the functional relationship between the particle size and the scattered light intensity received over a fixed solid angle. A significant difficulty arises when using laser beams with Gaussian (or other nonuniform) intensity profiles. The problem with detecting the peak value of the signal obtained from the scattered light is that this peak value is not only dependent upon the particle size, but also its trajectory through the measurement volume. Since the particle trajectories are random, an uncertainty in the measurement that must be resolved. When designing an in-situ nonintrusive device, this problem places constraints on the implementation of the technique in the field.

At least two viable methods have been proposed to deal with the problem of the Gaussian beam intensity distribution. Holve, D. J., and Self, S., "Optical Particle Sizing for In Situ Measurements", *Journal of Applied Optics*, Vol 18, No. 10, May 1979, pp. 1646–1652, utilized an inversion technique somewhat analogous to methods used in Computer Aided Tomography (CAT) systems. The numerical inversion scheme is used to unfold the dependence of the signals produced by light scattered by particles traversing the sample volume, formed by the laser beam and receiver optics, on random trajectories. A calibration procedure utilizing monodispersed particles of known size is used to define the sample volume and signal amplitude with respect to the particle size.

The second method for removing the ambiguity associated with the Gaussian beam intensity has been described by the inventor, W. D. Bachalo, in U.S. Pat. No. 4,329,054 which was issued on May 11, 1982. Subsequent disclosures of similar approaches have been described by R. J. Adrian in U.S. Pat. No. 4,387,993, issued June 14, 1983; by Apostolos Goulas, et al., in U.S. Pat. No. 4,348,111, issued Sept. 7, 1982; and R. A. Knollenberg in U.S. Pat. No. 4,636,075, issued Jan. 13, 1987. In each case, two concentric or coaxial beams are used having different wavelengths or polarizations. A beam having one wavelength or polarization is focused to a smaller diameter and directed to the center of a larger beam. In this way, the central uniform intensity of the larger beam may be identified. Only particles passing through the central portion of the larger beam will also produce signals on the small beam. When a signal is received from the small beam, the peak amplitude of the signal from the large beam is read and used to obtain the particle size. The method as described by Bachalo has the disadvantage of requiring a relatively large beam diameter ratio (5:1 to 7:1) between the small (pointer) and large (data) beams. A large beam diameter ratio is necessary to ensure that the incident intensity upon the particle from the large beam is known with sufficient accuracy. This requirement acts as a constraint on the upper limit of particle number densities (particle/cc) in which the system will operate satisfactorily.

Nonetheless, instruments based upon this concept have been developed by Hess and Spinoza (see U.S. Pat. No. 4,537,507, issued Aug. 27, 1985), and by Yeoman, M. L., Azzopardi, B. J., White, H. J., Bates, C. J., and Roberts, P. J., "Eng. Appl. of Laser Velocimetry", Winter Annual Meeting ASME, 1982. Upon careful calibration, the instruments were found to perform satisfactorily. As discussed by Bachalo, the method may be combined with the laser Doppler velocimeter to obtain simultaneous particle size and velocity measurements.

In the cases cited, the requirement for the rather large beam diameter ratios limits the application of the system to rather dilute particle fields. The method of Knollenberg which uses an elongated beam shape, overcomes this problem. However, the optical depth of field of the receiver and the need to measure particles on random trajectories also limits the application of the method.

The present invention discloses a means for significantly improving the above-mentioned technique to remove the serious limitation in high number density particle fields, presented by the need for large beam diameter ratios, allow the simultaneous measurement of particle size, speed, and the sample volume cross-section. A mathematical formulation is given to determine where each particle passed through the Gaussian beam intensity profile and hence, to determine the incident intensity upon the particle. In addition, determination of the individual particle trajectories will allow the measurement of the sample volume diameter for each particle size class. Finally, the particle trajectory through the sample volume along with the transit time will be demonstrated as a means for measuring the speed of the particle. The method has the significant advantage of requiring a beam diameter ratio of only two to three.

SUMMARY OF THE INVENTION

An apparatus for sizing particles, droplets, bubbles, or the like employing laser light scattering is disclosed. A laser is used for generating two beams of light having different wavelengths or polarizations. The beams with different wavelengths may be generated by an argon ion laser or by two different lasers (e.g. Helium Neon and Helium Cadmium). Two beams with orthogonal polarizaions may be produced by partitioning a single linearly polarized beam and rotating the polarization of one by 90°. One of the beams is then expanded using a conventional beam expander and then redirected to be coaxial with the first beam. The beams are then focused to a common focal region. One beam is from two to our times larger in diameter than the other. An optical collection apparatus for sensing the light scattered caused by the particles, droplets, bubbles or the like passing through the focused beams has an axis extending into the focused beams. The axis of the collection apparatus may be aligned with the transmitted beams in the forward or back direction (on-axis detection) or at some suitable angle to the beams (off-axis detection). The collection apparatus includes receiver lenses which focus the scattered light through the beam splitter onto a first photo-detector, and light reflected from the beam splitter is directed onto a second photo-detector. The photo-detectors sense the scattered light from the beams with separate wavelengths or polarizations and produce proportionate voltage amplitudes. The peak voltages are determined from the information sensed by the light collection apparatus. A mathematical formulation is used with the known beam diameters and intensities along with two measured signal voltage amplitudes to determine the particle trajectory through the beams and hence, particle size. The technique also allows for the determination of the sample volume cross-section and particle speed, thus allowing the determination of particle number density and volume flux.

BRIEF DESCRIPTION OF THE DRAWINGS

FIG. 6 is a graph illustrating a particle passing through the sample volume at a distance Xp from the center.

FIG. 7 is illustrates an end view of the sample volume and particle passing therethrough at a distance Xp from the center.

DETAILED DESCRIPTION OF THE INVENTION

An apparatus for sizing particles, droplets, bubbles, or the like (collectively "particles"), particularly suited for making in-situ nonintrusive measurements of the size, number density, and volume flux in a wide range of environments is disclosed. The apparatus utilizes known or predictable particle light scattering characteristics to obtain a size measurement from the measurement of the light scattering intensity. Ambiguity, associated with the Gaussian beam intensity and random particle trajectories through it, is eliminated with the use of a second coaxial beam having a smaller diameter. A mathematical analysis is provided to illustrate how this technique may be optimized such that the method can be used in high number density environments, and make efficient use of the available signals. In the following description, numerous specific details ae set forth such as wavelengths, beam diameter ratios, etc., however, it will be apparent to one skilled in the art that the invention may be practised without these specific details. In other instances, well known devices and components, structures and electrical processing circuits have not been described in detail in order to obscure the present invention unnecessarily.

Figure 1:
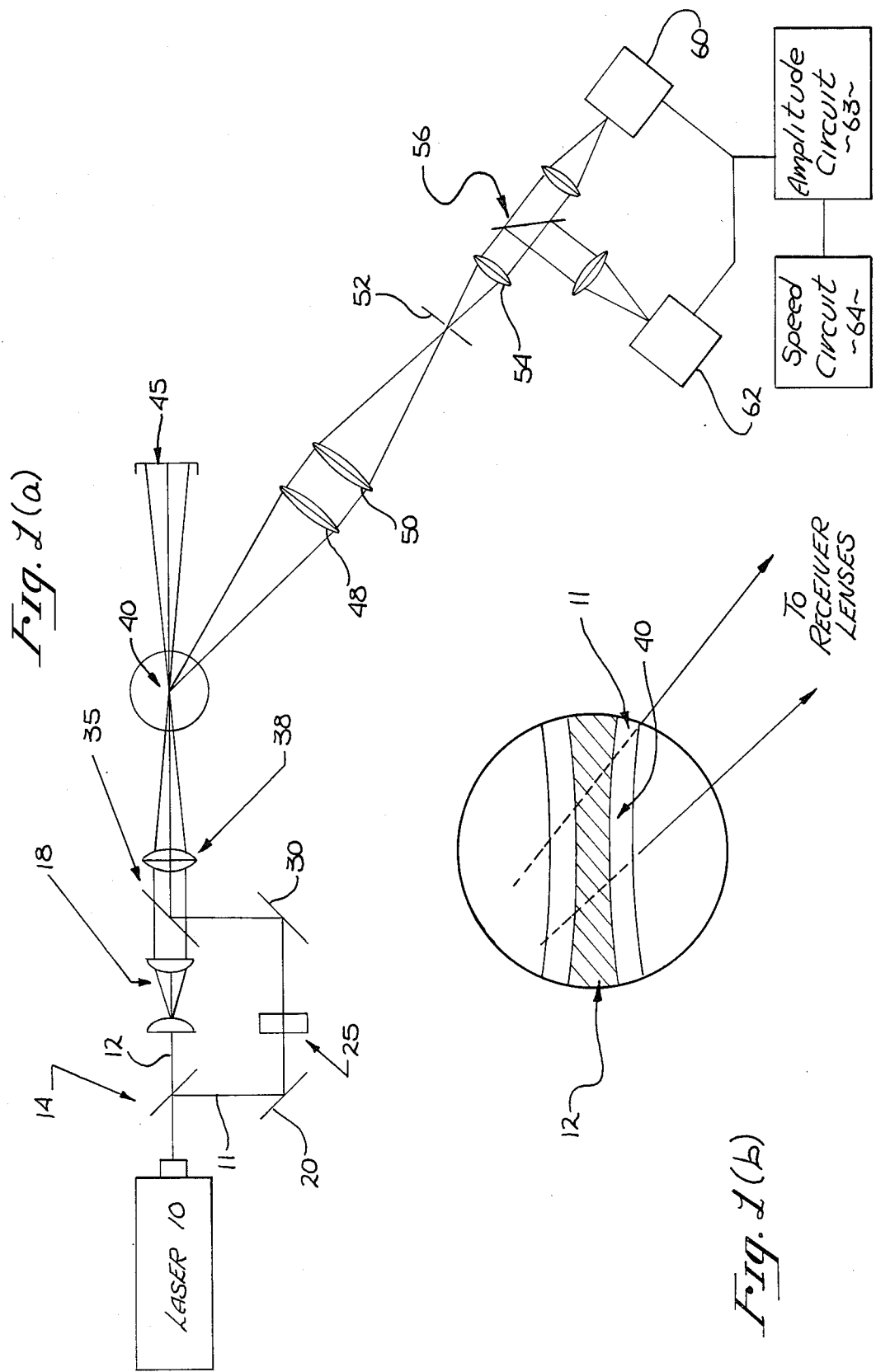
FIG. 1 is a schematic of the preferred optical system of the present invention.

Referring now to FIG. 1, the apparatus for determining the size of particles includes a laser 10. The laser beams employed by the present invention are generated, in the presently preferred embodiment, by a single laser 10 producing linearly polarized light. However, it will be appreciated that a laser capable of generating two wavelengths, or two separate lasers to provide two separate light wavelengths, could also be used. The light generated by laser 10 is partitioned into two beams 11 and 12 using a beam splitter 14. The beam 12 is increased in diameter using a beam expander denoted generally by the numeral 18. Beam 11 is directed by a reflector 20 through a polarization rotator 25 to rotate the polarization of beam 11 by 90°. The beam 11 is then directed by a reflector 30 to a second beam splitter 35 and made coaxial with the first beam 11. The coaxial beams 11 and 12 are then passed through a focusing lens 38 which causes the beams to focus at a common point. In the present embodiment, the beams 11 and 12 have orthogonal polarizations and the intensities are approximately equal. Where the light scattering by particles produces significant depolarization of the scattered light, different light wavelengths are utilized. As shown in FIG. 1 beams 11 and 12 are focused to form a sample volume 40. Beam stop 45 terminates beams 11 and 12 downstream from the sample volume 40. A light collection apparatus is provided for collecting the light scattered by particles passing through the sample volume 40. The collection apparatus includes receiver lenses 48 and 50 which define a solid angle of collection extending into the focused beams, and focus the scattered light through an aperture 52 and lens 54 onto a polarization beam splitter 56. Light passing through polarization beam splitter 56 is received by a first photo-detector 60, and light reflected off of beamsplitter 56 is received by photo-detector 62. Photo-detectors 60 and 62 are coupled to an amplitude circuit 63 which determines the proportionate voltage amplitudes. As will be described below, the proportionate voltages are used to determine particle trajectory through beams 11 and 12. The amplitude circuit 63 is coupled to a speed circuit 64, which as will be discussed, determines the speed of a particle passing through the sample volume 40.

The focused beams 11 and 12, as shown schematically, establish two confocal beam diameters. Note than in FIG. 1, the focused beams 11 and 12 have been shown in an enlarged form to illustrate the confocal beam pattern. As shown, beams 12 and 11 have opposite polarizations. Particles passing through the focused beams will scatter light with an intensity that is a function of their diameter and index of refraction, as well as the incident light intensity which is a function of their trajectory through the beams. As will be discussed, the amplitude of the light scattered simultaneously from both beams contains sufficient information to determine the particle size. This information may be predicted by the well-known Mie light scattering theory.

Figure 2:
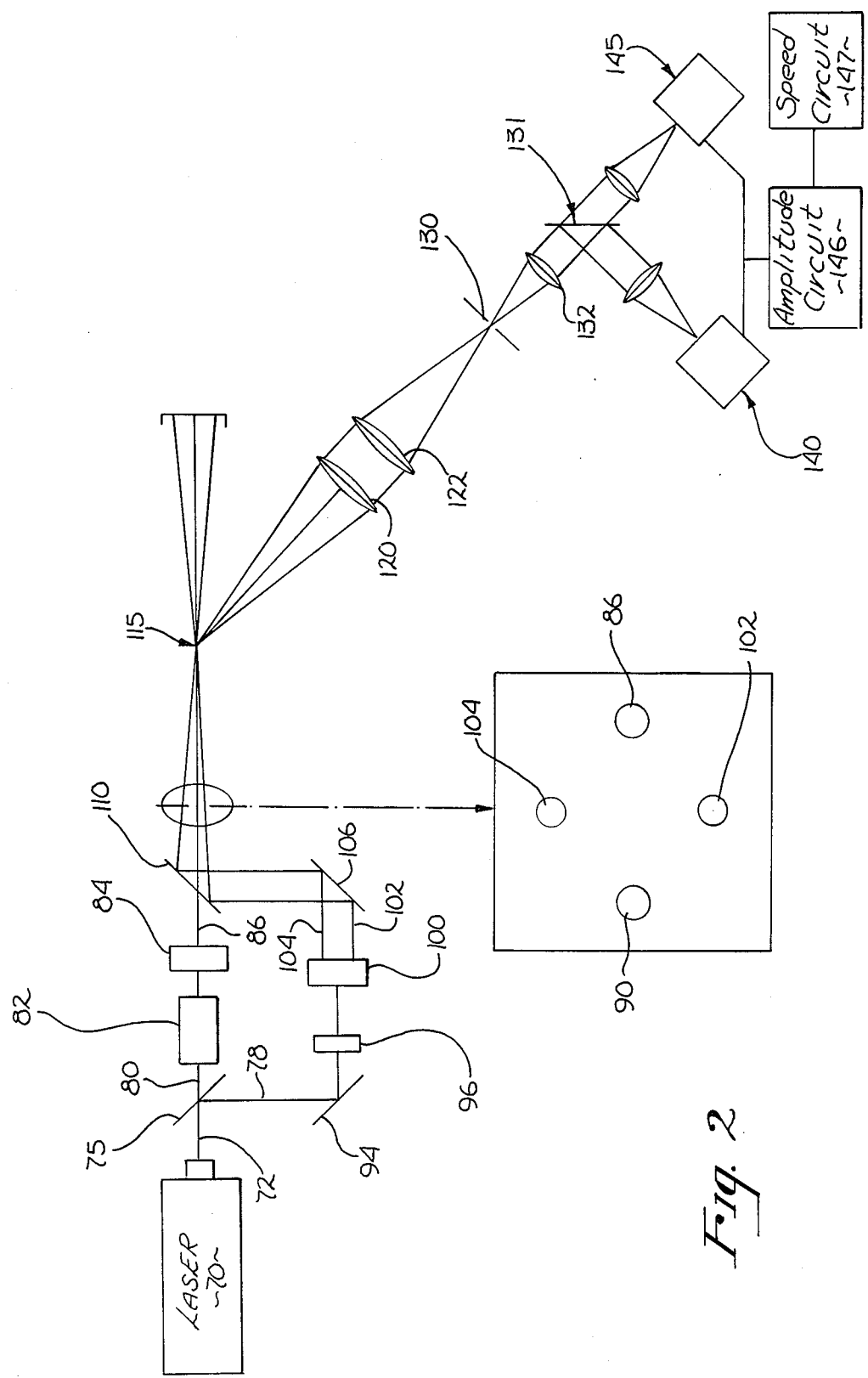
FIG. 2 is a schematic of an alternate optical system which incorporates the teachings of the present invention.

An alternative embodiment of the transmitting optics is shown in FIG. 2, which includes the use of beam splitters to form two pairs of beams that are oriented orthogonal to each other. A laser 70 generates a beam 72 which is directed onto a beamsplitter 75 forming two laser beams 78 and 80. Beam 80 is expanded by beam expander 82 with the now expanded beam split by a beam splitter 84 into two parallel beams 86 and 90. Beam 78 is directed by reflector 94 through a polarization rotator 96 and beam splitter 100 thereby forming two beams 102 and 104. Beams 102 and 104 are directed by reflector 106 onto beam combiner 110 such that a beam matrix results as shown in enlarged form in FIG. 2. These four beams 86, 90, 102 and 104, are then focused to a common crossover region thereby forming a sample volume 115. Particles passing through the focused beams will scatter light that form orthogonal interference fringes in the plane of the receiver lenses 120 and 122. The temporal frequency of this scattered light will be at the Doppler difference frequency. This is the well-known laser Doppler velocimeter technique. This technique can be incorporated with the present invention to provide the particle size and two components of the velocity vector in the plane orthogonal to the beam projection axis.

As shown in FIG. 2, the light scattering is sensed by a collection apparatus (as also disclosed in FIG. 1) which includes lenses 120 and 122 which define a solid angle of collection extending into two focused beams. This collection apparatus may be located at any preferred angle to the transmitted beams including the backscatter direction. The light scattered within the solid angle by particles passing through the sample volume 115 is collected and focused by the receiver lenses 120 and 122 onto an aperture 130. This aperture serves to admit only light scattered by particles crossing the laser beams in the appropriate region wherein they are completely focused. The intersection of the image of the aperture 130 and the focused laser beams serve to define the sample volume. The sample volume 115 is defined by the overlap of the focused laser beams and the image of the aperture in the collection apparatus. It is well known that the relative sample volume size will vary with the particle diameter, as will be discussed below.

In both the embodiments of FIGS. 1 and 2, the collected scattered light is, as will be discussed, focused onto photodetectors (in FIG. 1, detectors 62 and 60; in FIG. 2, detectors 140 and 145) which are coupled to a signal amplitude circuit 146 (FIG. 2) and 63 (FIG. 1). Sizing means (not shown) is coupled to the signal amplitude detection means in each embodiment for determining the size of the particles passing through the sample volume, as will be discussed, based upon the amplitudes of the collected signals. In addition, a speed circuit 64 (FIG. 1) and 147 (FIG. 2) is coupled to the signal amplitude detection means for determining the speed of the particle passing through the sample volume.

Figure 3:
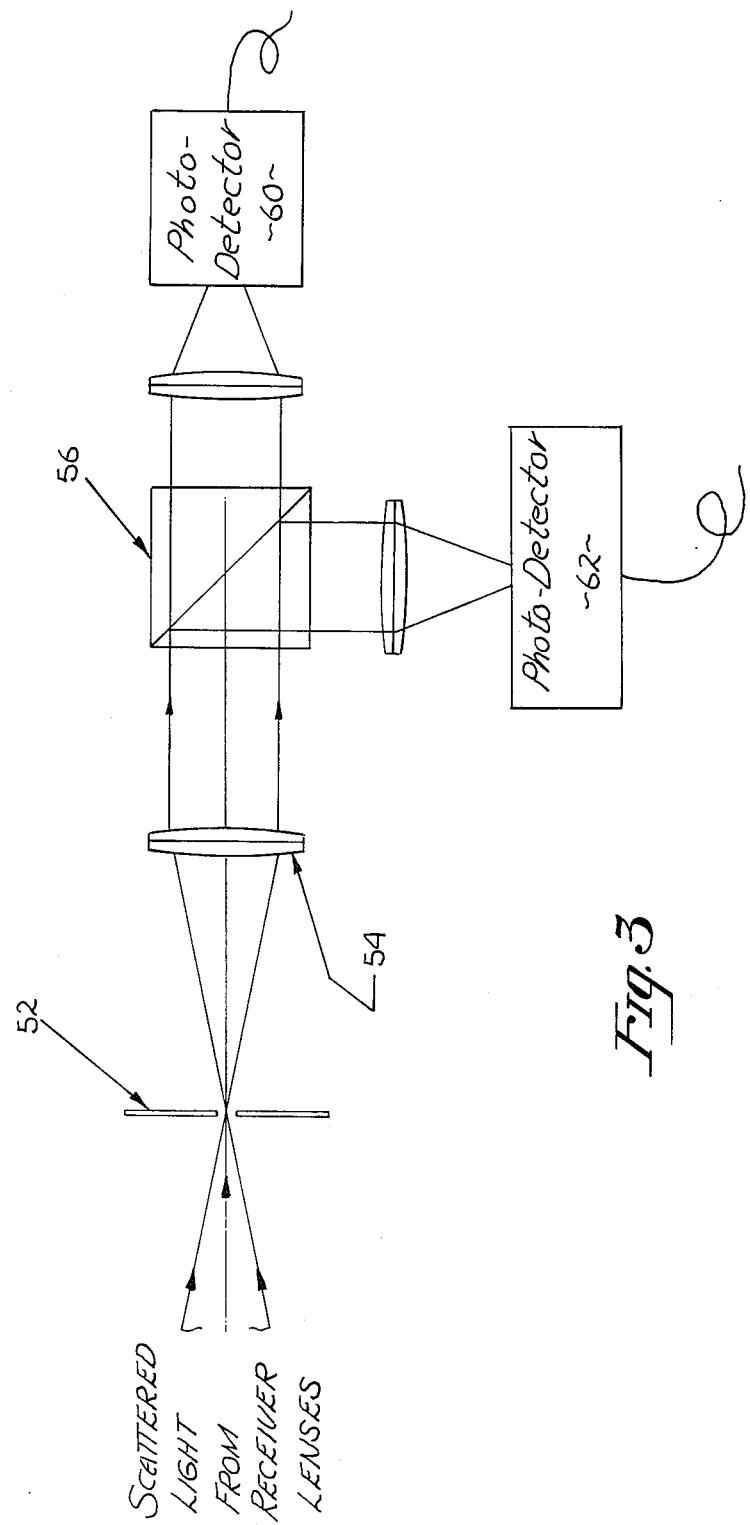
FIG. 3 is a more detailed schematic of the collection apparatus illustrated in FIGS. 1 and 2.

Referring now to FIG. 3, the collection apparatus of the present invention includes receiver lenses (lenses 48 & 50 in FIG. 1; lenses 120 and 122 in FIG. 2) which collect the scattered light onto the aperture 52 (130 in FIG. 2). As shown in FIG. 3, in both embodiments of FIGS. 1 and 2, a collimating lens 54 (132 in FIG. 2) disposed beyond the aperture is used to collimate the light before entering the polarizing beam splitter 56 (131 in FIG. 2) (a dichroic beam splitter is used if different wavelengths are used for the laser beams). Additional lenses may be used to focus the light onto the photodetectors. Thus, the receiver optics selectively separate light scattered from the small and large beams by their polarizations and direct the scattered light to their respectively photo-detectors. It will be appreciated that although the illustrated embodiments utilize a polarization beam splitter to separate the light scattering components, a variety of other means can be used. In addition, a combination of light wavelength and polarization could be utilized to ensure complete separation of the signals. For the purposes of the description below, references to optical elements will refer to the elements identified in FIG. 1, however, it will be appreciated that the methods described herein are equally applicable to the embodiment disclosed in FIG. 2.

The receiver system serves to produce two signals with amplitudes proportional to the particle diameter and the trajectory through the large beam 11 and small beam 12. These signals have nominal Gaussian shapes. The signals are coupled to linear preamplifiers that preserve the amplitude information, and amplitude circuit 63 determines the amplitude of the signals. These devices consist of well known electronic circuitry and are not described further in this Specification. Two simultaneous signals will only be accepted when the particle passes within the diameter of the small focused beam 12.

Figure 4:
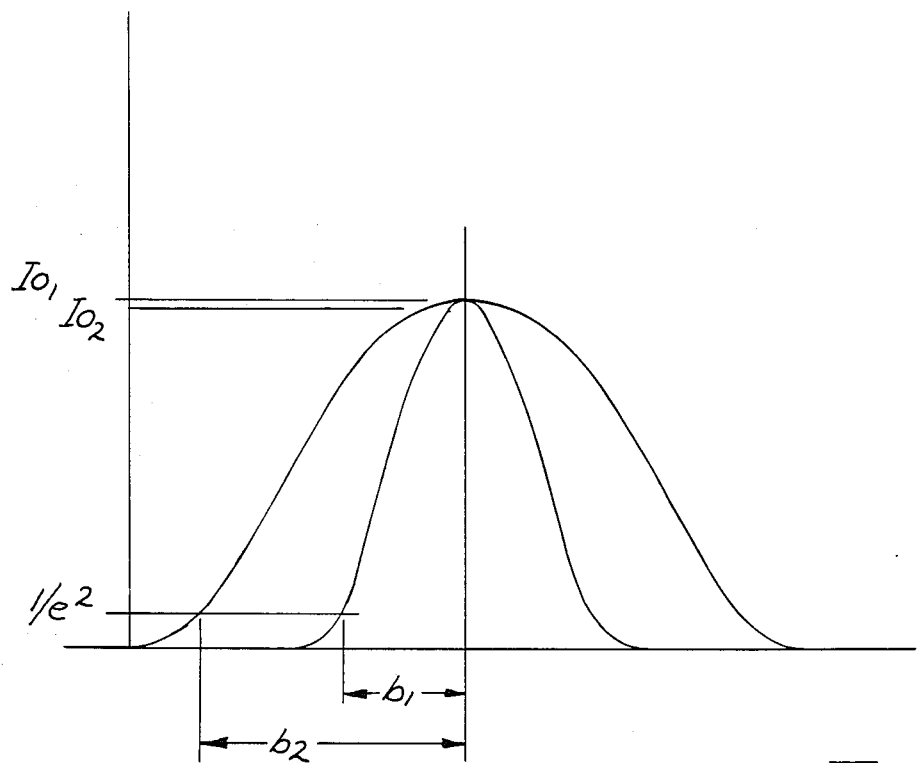
FIG. 4 is a graph of Gaussian beam intensity profiles of the first and second laser beams comprising the sample volume.
Figure 5:
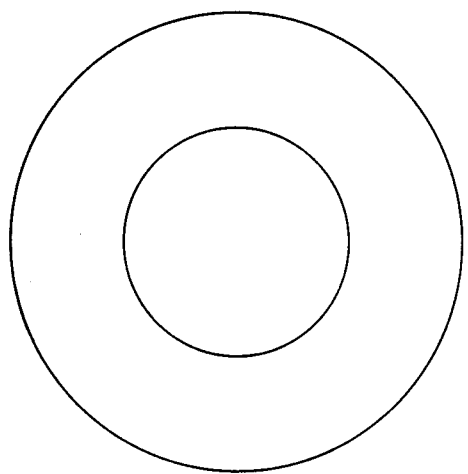
FIG. 5 is an end view of the sample volume of FIG. 4.

Referring briefly to FIG. 4, the beam intensities at the sample volume 40 is illustrated. As shown, distance $b_1$ is the distance from the maximum intensity of the central beam 12; and $b_2$ is the distance from the maximum intensity of beam 11, where the intensity falls to $I/e^2$ of the maximum. An end view of the sample volume 40 is shown in FIG. 5.

Referring now to FIGS. 6 and 7, a particle passing on an arbitrary path through small beam 12 will produce a signal from detectors 60 and 62 (in the embodiment of FIG. 2, detectors 140 and 145). In order to determine the incident intensity on the particle, the trajectory defined by the distance $x_p$ from the center of the Gaussian beam must be known. The well known equation describing the Gaussian beam intensity is given as $$I = I_o \exp[-2x^2/b^2]$$

where $I_o$ is the peak intensity of the beam which may be measured, x is the radius coordinate of the beam, and b is defined by convention as the radius wherein the intensity I is equal to $1/e$ ($e=2.7183$) of the peak intensity, $I_o$. The radius b may also be measured for each beam. Thus, for beams 11 and 12, the equations are:

$$I_{11} = I_{011} \exp[-2x_{11}^2/b_1^2]$$

$$I_{12} = I_{012} \exp[-2x_{12}^2/b_2^2]$$

where the subscripts 11 and 12 refer to beams 11 and 12 (or in the case of the embodiment of FIG. 2, beams 102/104 and 86/90, respectively). Considering now the light scattered by a particle, the scattering parameters $Q_{11}$ and $Q_{12}$ may be specified. These coefficients may be computed if the characteristics (shape and material) of the particles are known or they can be determined by calibration with samples which have predetermined sizes. The scattering coefficients depend on such well known parameters as diameter, index of refraction, incident light wavelength and polarization, angle of light collection, and shape of the particles. These scattering coefficients are generally computed or obtained by calibration as a function of the size of the particle such that if Q can be obtained, a look up table can then be used to obtain the diameter d. Thus, Q is specified as a function of d as Q(d).

Given an arbitrary particle path $x_p$ measured from the center of the beams and shown schematicaly in FIGs. 4, 5, 6 and 7, the scattered intensity may be expressed as:

$$I_{sca11} = I_{011} Q_{11}(d) \exp[-2x_p^2/b_1^2]$$

$$I_{sca12} = I_{012} Q_{12}(d) \exp[-2x_p^2/b_2^2]$$

Taking the ratio of the two equations yields:

$$I_{sca11}/I_{sca12} = \frac{I_{011} Q_{11}(d)}{I_{012} Q_{12}(d)} \exp\left[-2x_p^2\left(\frac{1}{b_1^2} - \frac{1}{b_2^2}\right)\right]$$

Solving for $x_p$ results in the following:

$$x_p = \left\{\frac{1}{2}\left(\frac{b_1^2 b_2^2}{b_1^2 - b_2^2}\right) \ln\left[\left(\frac{I_{sca11}}{I_{sca12}}\right)\left(\frac{I_{012}}{I_{011}}\right)\left(\frac{Q_{12}(d)}{Q_{11}(d)}\right)\right]\right\}^{1/2}$$

where ln is the natural logarithm. In this expression, the ratio $Q_{12}(d)/Q_{11}(d)$ may be determined easily by calculating the light scattering for the respective polarizations which is the only parameter that is different between the two quantities. The incident beam intensities, $I_{011}$ and $I_{012}$ are measured apriori. Measurements of $I_{sca11}$ and $I_{sca12}$ are made for each particle based on the signal measurements. Thus, $x_p$ can be obtained explicitly from the measured quantities for each particle size and trajectory. With xp determined, the equations may be rearranged as $$Q_{11}(d) = \frac{I_{sca11}}{I_{011}} \exp[-2x_p^2/b_1^2]$$

$$Q_{12}(d) = \frac{I_{sca11}}{I_{012}} \exp[-2x_p^2/b_2^2]$$

to obtain $Q_{11}(d)$ and $Q_{12}(d)$. These values are then used in the respective lookup tables to obtain redundant measurements of the diameter of the particles. As mentioned, the lookup tables can be generated using the Mie theory or by direct calibration. Even if the Mie theory is used, calibration is still required to determine the constants that describe the collection efficiencies and gains of the system. This requirement and procedure is well-known.

Particles scatter as a function of their diameter. For example, for particles, the scattered light intensity increases approximately with the diameter squared. Since a scattered light level above a given threshold level must be scattered before the particle is detected, this will set an extreme radius within which the particle must pass before it is detected. The other dimension of the sample volume is set by the image of the receiver aperture. Because of the Gaussian incident intensity distribution (see FIGS. 4 and 6), the maximum radius for detection will be a function of the particle size. This change in the sampling cross section must be taken into account to prevent biasing the measured size distribution towards the large particles which have an effectively larger target for detection.

Using the aforementioned technique for determining the radius of the particle trajectory, $x_p$, a statistical distribution of the radii may be formed for each particle diameter. From this, the maximum radii for each partical diameter $x_{max}(d)$ can be determined which then defines the sampling cross section for each particle size measured. This method also includes any variances that may arise as a result of the measurement environment. The above mentioned sampling cross-section bias is then removed by multiplying the number of samples, n(d), for each particle size class in the measured statistical distribution by the ratio of the largest sampling cross section to that of the respective particle size as:

$$n(d)_c = \frac{x_{max}(d_{max}) \cdot n(d)}{x_{max}(d)}$$

where $d_{max}$ is the largest size in the distribution. The average radii for each size class may also be used for this purpose and, in fact, is more reliable considering the statistics.

Knowledge of the radii of particle transit also provides necessary information for obtaining the particle's speed. Since the focused beam is circular, the path length through the beam as shown in FIG. 6 is known. The path length between the points where the signal exceeds a threshold level and where it falls below the threshold is determined as:

$$T = Q_1(d) I_{01} \exp[-2x_t^2/b_1^2]$$

where T is the set threshold level and $x_t$ is the beam radius at the intensity level that produces a signal to the threshold level. Based on the analyses to this point, Q(d), $b_1$, and $I_o$ are known. Therefore, the equation can be used to solve for $x_t$ given as:

$$x_t = b_1\left[\frac{1}{2} \ln\left(\frac{T}{Q_1(d) \cdot I_{01}}\right)\right]$$

The particle path length between where the signal exceeds the threshold to where it falls below is given simply as:

$$l = 2[x_t^2 - x_p^2]^{\frac{1}{2}}$$

where $x_p$ and $x_t$ are deduced from the above relationships. A counter and a fixed frequency clock is used to measure the time, t, between when the signal exceeds the threshold to where it falls below the threshold again. The particle speed is then obtained as $$S = X_t/t$$

The second approach illustrated in FIG. 2 utilizes the interference fringes formed by the pairs of crossed beams to obtain two components of particle velocity. This method consists of the well-known laser Doppler velocimeter (LDV) method. Combining this method with the present method allows the simultaneous measurement of particle size and velocity.

Figure 8:
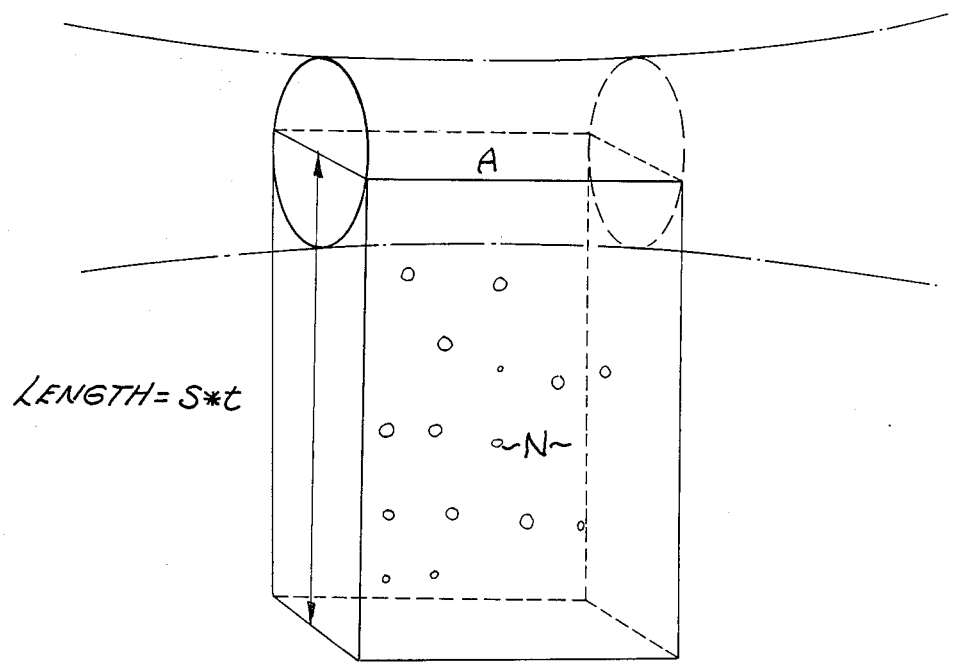
FIG. 8 illustrates the volume swept by particles passing through the sample volume in time t.

Given the measurements of the particle speed, sampling cross section, and number of particles counted per second, the particle number density can be obtained. This is accomplished by determining a swept volume as shown in FIG. 8 with a cross-sectional area defined by the sampling cross section and a length given by S multiplied by t, where t is the sampling time. For accuracy, the sample volume and speed must be determined for each particle size. The number density is then given as:

$$N = \sum_{i=1}^{m} \frac{n_i(d)}{A_i(d) \cdot S_i(d) \, t}$$

where $n_i(d)$ is the number of particles in each size class i of which there are m size classes, $A_i(d)$ is the corresponding sampling cross-sectional area for particle size d, $S_i(d)$ is the speed of particle size class d.

Other useful parameters may be extracted given the above parameters. Thus, the system revealed provides a versatile measurement technique for particle field diagnostics. Although the present invention has been described with reference to FIGS. 1–8, it will be appeciated that the Figures are for illustration only, and are not limitations on the invention. Numerous other optical structures and arrangements may be used which incorporate the teachings of the present invention as disclosed herein.

I claim:

1. An apparatus employing laser light scattering for determining the size of a particle, comprising:

laser beam generation means for generating first and second laser beams having Gaussian beam intensities;

beam expansion means in optical alignment with said first laser beam for expanding the diameter of said first beam;

light directing means for directing said first and second beams and combining said beams such that said second beam is disposed within and coaxial with said first beam;

focussing means in optical alignment with said light directing means for focussing said first and second beams such that they converge and said first beam is disposed within and coaxial with said second beam, thereby forming a sample volume;

collection means for sensing light scattered by a particle passing through said sample volume, said collection means converting said scattered light into electrical signals;

amplitude means coupled to said collection means for determining the amplitude of said electrical signals representing said scattered light;

trajectory determining means coupled to said amplitude means for calculating the trajector ($x_p$) of a particle passing through said sample volume, said trajectory being defined by:

$$x_p = \left\{ \frac{1}{2} \frac{(b_1^2 \, b_2^2)}{(b_1^2 - b_2^2)} \ln \left[ \frac{(I_{sca1})}{I_{sca2}} \frac{(I_{o2})}{I_{o1}} \frac{(Q_2(d))}{Q_1(d)} \right] \right\}^{\frac{1}{2}}$$

where:
$x_p$ = distance from the center of said second beam in said sample volume;
$b_1$ = distance from the maximum intensity of said second beam in said sample volume;
$b_2$ = distance from the maximum intensity of said first beam in said sample volume;
$I_{o1}$ = peak intensity of said first beam;
$I_{o2}$ = peak intensity of said second beam;
$I_{sca1}$ = scattered light intensity of said first beam;
$I_{sca2}$ = scattered light intensity of said second beam;
$Q_1$ = scattering parameter of said first beam;
$Q_2$ = scattering parameter of said second beam;
sizing means coupled to said trajectory determining means for determining the diameter of said particle from said particle's trajectory;
whereby the size of said particle is determined.

2. The apparatus as defined by claim 1, wherein said $I_{sca1}$ and $I_{sca2}$ values are determined by said trajectory determining means from the expressions:

$$I_{sca1} = I_{o1} Q_1(d) \exp[-2x_p^2/b_1^2]$$

$$I_{sca2} = I_{o2} Q_2(d) \exp[-2x_p^2/b_2^2].$$

3. The apparatus as defined by claim 2, wherein said sizing means includes look-up table means for relaing said $Q_1(d)$ and $Q_2(d)$ values to said particle diameter (d), such that inputting said $Q_1(d)$ and $Q_2(d)$ values into said look-up table means results in an output corresponding to a diameter (d).

4. The apparatus as defined by claim 3, further including speed means coupled to said amplitude means for determining the speed of said particle passing through said sample volume.

5. The apparatus as defined by claim 4, wherein said collection means includes first and second photo-detectors for sensing light scattered by said particle through each of said first and second beams, respectively, said photo-detectors being coupled to said amplitude means.

6. The apparatus as defined by claim 5, wherein said photo-detectors sense said scattered light once said light exceeds a threshold value defined as:

$$T = Q_1(d) I_{o1} \exp[-2x_t^2/b_1^2]$$

where:
T = threshold value;
$x_t$ = beam radius at the intensity level which produces a signal at said threshold level.

7. The apparatus as defined by claim 6, wherein the path length of said particle between where said electrical signals exceeds said threshold levels to where said signals fall below said level is defined as:

$$l = 2[x_t^2 - x_p^2]^{\frac{1}{2}}.$$

8. The apparatus as defined by claim 7, wherein said speed means determines the time t when said signal exceeds said threshold value, the speed(s) of said particle being defined as:

$$X = x_t/t.$$

9. The apparatus as defined by claim 8, wherein said speed means further determines the number of density of particles passing through said sample volume from the expression:

$$N = \sum_{i=1}^{M} \frac{n_i(d)}{A_i(d) \cdot S_i(d)t}$$

where:
N = number density of said particles;
$n_i(d)$ = number of particles in each size class i of M size classes;
$A_i(d)$ = sample cross-section area for particle class size d;
$S_i(d)$ = speed of particle in size class d.

10. An apparatus employing laser light scattering for determining the size of a particle, comprising:
laser beam generation means for generating first and second laser beams hving Gaussian beam intensities;
beam expansion and splitting means in optical alignment with said first laser beam for expanding the diameter of said first beam and splitting said first beam into at least two parallel coplaner beams disposed in a first plane;
polarization and beam splitting means in optical alignment with said second beam and splitting said second beam into at least two parallel coplanar beams disposed in a second plane;
light detecting means for directing said first and second beam such that said first plane is disposed approximately at a known angle with respect to said second plane;
focussing means in optical alignment with said light directing means for focussing said first and second beams such that they converge thereby forming a sample volume;
collection means for sensing light scattered by a particle passing through said sample volume, said collection means converting said scattered light into electrical signals;
amplitude means coupled to said collection means for determining the amplitude of said electrical signals representing said scattered light;
trajectory determining means coupled to said amplitude means for calculating the trajectory ($x_p$) of a particle passing through said sample volume, said trajectory being defined by:

$$x_p = \left\{ \frac{1}{2} \frac{(b_1^2 \, b_2^2)}{(b_1^2 - b_2^2)} \ln \left[ \frac{(I_{sca1})}{I_{sca2}} \frac{(I_{o2})}{I_{o1}} \frac{(Q_2(d))}{Q_1(d)} \right] \right\}^{\frac{1}{2}}$$

where:
$x_p$ = distance from the center of said second beam in said sample volume;
$b_1$ = distance from the maximum intensity of said second beam in said sample volume;
$b_2$ = distance from the maximum intensity of said first beam in said sample volume;
$I_{o1}$ = peak intensity of said first beam;
$I_{o2}$ = peak intensity of said second beam;
$I_{sca1}$ = scattered light intensity of said first beam;
$I_{sca2}$ = scattered light intensity of said second beam;
$Q_1$ = scattering parameter of said first beam;
$Q_2$ = scattering parameter of said second beam;
sizing means coupled to said trajectory determining means for determining the diameter of said particle from said particle's trajectory;
whereby the size of said particle is determined.

11. The apparatus as defined by claim 10, wherein said $I_{sca1}$ and $I_{sca2}$ values are determined by said trajectory determining means from the expressions:

$$I_{sca1} = I_{o1} Q_1(d) \exp[-2x_p^2/b_1^2]$$

$$I_{sca2} = I_{o2} Q_2(d) \exp[-2x_p^2/b_2^2].$$

12. The apparatus as defined by claim 11, wherein said sizing means includes look-up table means for relating said $Q_1(d)$ and $Q_2(d)$ values to said particle diameter (d), such that inputting said $Q_1(d)$ and $Q_2(d)$ values into said look-up table means results in an output corresponding to a diameter (d).

13. The apparatus as defined by claim 12, further including speed means coupled to said amplitude means for determining the speed of said particle passing through said sample volume.

14. The apparatus as defined by claim 13, wherein said collection means includes first and second photo-detectors for sensing light scattered by said particle through each of said first and second beams, respectively, said photo-detectors being coupled to said amplitude means.

15. The apparatus as defined by claim 14, wherein said photo-detectors sense said scattered light once said light exceeds a threshold value defined as:

$$T = Q_1(d) I_{o1} \exp[-2x_t^2/b_1^2]$$

where:
T = threshold value;
$x_t$ = beam radius at the intensity level which produces a signal at said threshold level.

16. The apparatus as defined by claim 15, wherein the path length of said particle between where said electrical signals exceeds said threshold levels to where said signals fall below said level is defined as:

$$l = 2[x_t^2 - x_p^2]^{\frac{1}{2}}.$$

17. The apparatus as defined by claim 16, wherein said speed means determines the two orthogonal velocity components using a laser Doppler velocimeter.

18. The apparatus as defined by claim 17, wherein said known angle is 90°.

19. The apparatus as defined by claim 17, wherein said speed means further determines the number density of particles passing through said sample volume from the expression:

$$N = \sum_{i=1}^{M} \frac{n_i(d)}{A_i(d) \cdot S_i(d)t}$$

where:
N = number density of said particles;

$n_i(d)$ = number of particles in each size class i of M size classes;

$A_i(d)$ = sample cross-section area for particle class size d;

$S_i(d)$ = speed of said particle in size class d.

20. A method employing laser light scattering for determining the size and trajectory of a particle comprising the steps of generating first and second laser beams having Gaussian beam intensities;

expanding the diameter of said first beam;

directing said first and second combining said beams such that said second beam is disposed within and coaxial with said first beam;

focussing said first and second beam such that they converge, thereby forming a sample volume;

sensing light scattered by a particle passing through said sample volume, and converting said scattered light into electrical signals;

determining the amplitude of said electrical signals representing said scattered light;

determining the trajectory ($x_p$) of a particle passing through said sample volume, said trajectory being defined by $$x_p = \left\{ \frac{1}{2} \frac{(b_1^2 \, b_2^2)}{(b_1^2 - b_2^2)} \ln \left[ \frac{(I_{sca1})}{I_{sca2}} \frac{(I_{o2})}{I_{o1}} \frac{(Q_2(d))}{Q_1(d)} \right] \right\}^{\frac{1}{2}}$$

where:

$x_p$ = distance from the center of said second beam in said sample volume;

$b_1$ = distance from the maximum intensity of said first beam in said sample volume;

$b_2$ = distance from the maximum intensity of said second beam in said sample volume;

$I_{o1}$ = peak intensity of said first beam;

$I_{o2}$ = peak intensity of said second beam;

$I_{sca1}$ = scattered light intensity of said first beam;

$I_{sca2}$ = scattered light intensity of said second beam;

$Q_1$ = scattering parameter of said first beam;

$Q_2$ = scattering parameter of said second beam;

determining the diameter of said particle from said particle's trajectory;

whereby the size and trajectory of said particle is determined.

21. The method as defined by claim 20, wherein said $I_{sca1}$ and $I_{sca2}$ values are determined by said trajectory determining means from the expressions:

$$I_{sca1} = I_{o1} Q_1(d) \exp[-2x_p^2/b_1^2]$$

$$I_{sca2} = I_{o2} Q_2(d) \exp[-2x_p^2/b_2^2].$$

22. The method as defined by claim 20, wherein said size of said particle is determined using look-up table means for relating said $Q_1(d)$ and $Q_2(d)$ values to said particle diameter d such that inputting said $Q_1(d)$ and $Q_2(d)$ values into said look-up table means results in an output corresponding to a diameter d.

23. The method as defined by claim 21, further including the step of determining the speed of said particle passing through said sample volume.

24. The method as defined by claim 22, wherein said sensing step includes the use of first and second photo-detectors.

25. The method as defined by claim 23, wherein said collection means includes first and second photo-detectors for sensing light scattered by said particle through each of said first and second beams, respectively, said photo-detectors being coupled to said amplitude means.

26. The method as defined by claim 24, wherein said photo-detectors sense said scattered light once said light exceeds a threshold value defined as:

$$T = Q_1(d) I_{o1} \exp[-2x_t^2/b_1^2]$$

where:

T = threshold value;

$x_t$ = beam radius at the intensity level which produces a signal at said threshold level.

27. The method as defined by claim 25, wherein the path length of said particle between where said electrical signals exceeds said threshold levels to where said signals fall below said level is defined as:

$$I = 2[x_t^2 - x_p^2]^{\frac{1}{2}}.$$

28. The method as defined by claim 26, wherein said speed means determines the time t when said signal exceeds said threshold value, the speed(s) of said particle being defined as:

$$S = x_t/t.$$

* * * * *

UNITED STATES PATENT AND TRADEMARK OFFICE
CERTIFICATE OF CORRECTION

PATENT NO. : 4,854,705
DATED : 8/8/89
INVENTOR(S) : Bachalo

It is certified that error in the above-identified patent and that said Letters Patent is hereby corrected as shown below:

col. 11, line 07    delete "X"    insert --S--

Signed and Sealed this

Ninth Day of April, 1991

*Attest:*

HARRY F. MANBECK, JR.

*Attesting Officer*    *Commissioner of Patents and Trademarks*